United States Patent
Sofer et al.

(10) Patent No.: US 10,504,805 B2
(45) Date of Patent: Dec. 10, 2019

(54) METHOD OF EXAMINING DEFECTS IN A SEMICONDUCTOR SPECIMEN AND SYSTEM THEREOF

(71) Applicant: Applied Materials Israel Ltd., Rehovot (IL)

(72) Inventors: Yotam Sofer, Givatayim (IL); Ariel Hirszhorn, Ness-Ziona (IL)

(73) Assignee: Applied Materials Israel Ltd., Rehovot (IL)

( * ) Notice: Subject to any disclaimer, the term of this patent is extended or adjusted under 35 U.S.C. 154(b) by 82 days.

(21) Appl. No.: 15/685,781

(22) Filed: Aug. 24, 2017

(65) Prior Publication Data
US 2019/0067134 A1 Feb. 28, 2019

(51) Int. Cl.
| | |
|---|---|
| *G06K 9/00* | (2006.01) |
| *H01L 21/66* | (2006.01) |
| *G01N 15/14* | (2006.01) |
| *G05B 19/418* | (2006.01) |

(52) U.S. Cl.
CPC ......... *H01L 22/24* (2013.01); *G01N 15/1456* (2013.01); *G05B 19/41875* (2013.01); *H01L 22/12* (2013.01); *H01L 22/20* (2013.01)

(58) Field of Classification Search
CPC ..... H01L 23/498; H01L 21/66; H01L 21/302; H01L 22/20; H01L 22/24; G06F 19/00; G02F 1/29; G01N 21/88; G01N 21/00; G01N 21/9501; G01N 21/27; G01N 21/55; G01N 2021/1748; G01N 15/1456
See application file for complete search history.

(56) References Cited

U.S. PATENT DOCUMENTS

| | | | | |
|---|---|---|---|---|
| 5,828,778 A * | 10/1998 | Hagi | ............ | G06T 7/0004 382/145 |
| 6,914,670 B1 * | 7/2005 | Almogy | ............ | G01N 21/9501 356/236 |
| 7,161,669 B2 * | 1/2007 | Velidandla | ............ | G01B 11/303 257/E21.53 |
| 7,440,093 B1 * | 10/2008 | Xiong | ............ | G01N 21/9501 250/559.39 |
| 7,684,032 B1 * | 3/2010 | Meeks | ............ | G01N 21/9501 356/237.2 |
| 8,143,078 B2 * | 3/2012 | Libbert | ............ | H01L 22/24 257/E21.527 |

(Continued)

*Primary Examiner* — Amir Alavi
(74) *Attorney, Agent, or Firm* — Lowenstein Sandler LLP (57) ABSTRACT

There is provided a method of examining defects in a semiconductor specimen and a system thereof. The method comprises: processing a first defect map obtained for a first semiconductor specimen to assign cluster-seed (CS) scores to at least some of the classified defects presented therein, wherein a CS score of a given defect is indicative of a number of neighboring defects classified to the same class as the given defect; upon obtaining a second defect map for a second semiconductor specimen, using the CS scores assigned to the at least some of the classified defects presented in the first defect map to select, among defects presented in the second defect map, defects for review, wherein the first defect map and the second defect map present respective defects in an attribute hyperspace; and reviewing defects selected in the second defect map, thereby obtaining classified defects presented in the second semiconductor specimen.

20 Claims, 6 Drawing Sheets

(56) References Cited

U.S. PATENT DOCUMENTS

| | | | |
|---|---|---|---|
| 8,164,598 B2* | 4/2012 | Kimpe | G09G 3/20 345/629 |
| 8,255,172 B2* | 8/2012 | Auerbach | G01N 21/9501 702/35 |
| 8,664,596 B2* | 3/2014 | Zhao | G01N 23/225 250/306 |
| 2008/0089561 A1* | 4/2008 | Zhang | G06K 9/00228 382/118 |
| 2010/0327451 A1* | 12/2010 | Chou | G03F 7/70633 257/770 |

* cited by examiner

METHOD OF EXAMINING DEFECTS IN A SEMICONDUCTOR SPECIMEN AND SYSTEM THEREOF

TECHNICAL FIELD

The presently disclosed subject matter relates, in general, to the field of examination of a specimen, and more specifically, to methods and systems for automating of a specimen's examination.

BACKGROUND

Current demands for high density and performance, associated with ultra large scale integration of fabricated devices, require submicron features, increased transistor and circuit speeds, and improved reliability. Such demands require formation of device features with high precision and uniformity, which, in turn, necessitate careful monitoring of the fabrication process, including frequent and detailed inspection of the devices while they are still in the form of semiconductor wafers.

The term "specimen" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles.

The term "defect" used in this specification should be expansively construed to cover any kind of abnormality or undesirable feature formed on or within a wafer.

The complex manufacturing process of objects is not error-free and such errors may cause faults in the manufactured objects. The faults may include defects that can harm operation of the object, and nuisances, which may be defects, but do not cause any harm or malfunction of the manufactured unit. By way of non-limiting examples, defects may be caused during the manufacturing process, due to faults in the raw material; mechanical, electrical or optical errors; human errors or others. Further, defects may be caused by spatio-temporal factors, such as temperature changes of the wafer occurring after one or more manufacturing stages during the examination process, which may cause some deformations of the wafer. The examination process can also introduce further alleged errors, for example due to optical, mechanical or electrical problems in the examination equipment or process, which thus provide imperfect captures. Such errors may produce false positive findings, which may seem to contain a defect, but no actual defect exists at the area.

In many applications, the type, or class, of a defect is of importance. For example, defects may be classified into one of a number of classes, such as a particle, a scratch, process, or the like.

Unless specifically stated otherwise, the term "examination" used in this specification should be expansively construed to cover any kind of detection and/or classification of defects in an object. Examination is provided by using non-destructive examination tools during or after manufacture of the object to be examined. By way of non-limiting example, the examination process can include scanning (in a single or in multiple scans), sampling, reviewing, measuring, classifying and/or other operations provided with regard to the object or parts thereof, using one or more examination tools. Likewise, examination can be provided prior to manufacture of the object to be examined and can include, for example, generating an examination recipe(s). It is noted that, unless specifically stated otherwise, the term "examination" or its derivatives used in this specification are not limited with respect to the size of the inspected area(s), to the speed or resolution of the scanning or to the type of examination tools. A variety of non-destructive examination tools includes, by way of non-limiting example, optical tools, scanning electron microscopes, atomic force microscopes, etc.

Examination process can include a plurality of examination steps. During the manufacturing process, the examination steps can be performed a multiplicity of times, for example after the manufacturing or processing of certain layers, or the like. Additionally or alternatively, each examination step can be repeated multiple times, for example for different wafer locations or for the same wafer locations with different examination settings.

By way of non-limiting example, run-time examination can employ a two-step procedure, e.g. inspection of a specimen followed by review of sampled defects. During the inspection step, the surface of a specimen or a part thereof (e.g. areas of interest, hot spots, etc.) is typically scanned at relatively high-speed and/or low-resolution. The captured inspection image is analyzed in order to detect defects and obtain locations and other inspection attributes thereof. At the review step the images of at least part of defects detected during the inspection phase are, typically, captured at relatively low speed and/or high-resolution, thereby enabling classification and, optionally, other analyses of the at least part of defects. In some cases both phases can be implemented by the same inspection tool, and, in some other cases, these two phases are implemented by different inspection tools.

GENERAL DESCRIPTION

In accordance with certain aspect of the presently disclosed subject matter, there is provided an examination system comprising:
a processing and memory circuitry (PMC) configured to:
  upon obtaining a first defect map representing defects in a first semiconductor specimen in an attribute hyperspace, process the first defect map to assign cluster-seed (CS) scores to at least part of classified defects presented therein, wherein a CS score of a given defect is indicative of a number of neighboring defects classified to the same class as the given defect;
  upon obtaining a second defect map representing defects in a second semiconductor specimen in the attribute hyperspace, use the CS scores assigned to the at least part of classified defects presented in the first defect map to select, among defects presented in the second defect map, defects for review; and
an examination tool configured to review defects selected in the second defect map, thereby enabling classification thereof.

The defect maps can be obtained with a help of inspection tool configured to capture a first image of a first semiconductor specimen and a second image of a second semiconductor specimen, wherein the first image is informative of values usable for obtaining the first defect map and the second image is informative of values usable for obtaining the second defect map.

Using the CS scores can comprise: applying to the second defect map a set of one or more sampling utilities, each providing, for a given defect, a respective score, thereby obtaining for the given defect a set of one or more sampling scores, wherein the set of sampling scores comprises a score obtained by using CS scores of defects in the first semiconductor specimen and provided by a CS score-based utility; calculating a resulting "review" score of the given defect as a function of weighed sampling scores; and selecting the defects for review in accordance with the resulting "review" scores.

The PMC can be further configured to use the CS scores assigned to the at least part of classified defects presented in the first defect map to generate a sampling recipe usable for selecting defects in the second semiconductor specimen for reviewing by the examination tool. Optionally, the PMC can be further configured to generate the CS score-based utility, and to use the generated utility to generate the sampling recipe.

The system can further comprise a recipe node operatively connected to the examination tool, wherein the PMC can be implemented as a part of the recipe node.

In accordance with another aspect of the presently disclosed subject matter, there is provided a method comprising:

processing by a processing and memory circuitry (PMC), a first defect map obtained for a first semiconductor specimen to assign cluster-seed (CS) scores to at least part of the classified defects presented therein, wherein a CS score of a given defect is indicative of a number of neighboring defects classified to the same class as the given defect;

upon obtaining a second defect map for a second semiconductor specimen, using, by the PMC, the CS scores assigned to the at least part of classified defects presented in the first defect map to select, among defects presented in the second defect map, defects for review, wherein the first defect map and the second defect map present respective defects in an attribute hyperspace; and reviewing defects selected by the PMC in the second defect map, thereby obtaining classified defects presented in the second semiconductor specimen.

The method can further comprise: applying to the second defect map the set of sampling utilities to select a first subgroup of defects for review, wherein the set of sampling utilities comprises two or more sampling utilities; and upon classifying defects in the first subgroup, repeating until a stop condition is fulfilled: modifying the set of sampling utilities to reduce the weight of the score obtained by using CS scores of defects in the first semiconductor specimen; applying to the second defect map a modified set of sampling utilities to select a next subgroup of defects for review; and classifying defects in the next subgroup.

The method can further comprise: upon classifying defects presented in the second defect map, assigning to said classified defects respective CS scores; accumulating CS scores assigned to defects in the first and the second defect maps; using the accumulated CS scores to select, among defects presented in a next defect map, defects for review; upon classifying defects in the next defect map, processing the next defect map to assign CS scores to the classified defects respectively presented therein; accumulating CS scores assigned to defects in the first defect map, the second defect map and the next defect map, said accumulated CS scores usable for selecting defects for review in a further next defect map.

In accordance with further aspects of the presently disclosed subject matter, selecting in the second defect map defects for review can comprise assigning scores to defects presented therein and selecting defects matching a predefined score-related criterion, wherein the scores are calculated using the CS scores assigned to the at least part of the classified defects presented in the first defect map. Optionally, score-related criterion can specify a number of top-ranked defects to be selected in accordance with a predefined number of defects to be selected for review.

Selecting, among defects presented in the second defect map, defects for review can comprise: selecting, among defects presented in the first defect map, defects having assigned CS score and meeting one or more predefined rules, thus giving rise to seed defects; for each given seed defect: identifying a virtual location of the given seed defect in the second defect map; identifying in the second defect map a predefined number of neighboring defects being the nearest neighbors to the virtual location of the given seed defect; assigning to each identified neighboring defect an intermediate "seed" score being in direct relationship with CS score of the given seed defect and in inverse relationship with the distance between the respective virtual location and the neighboring defect; for each defect identified in the second defect map as a neighboring defect of at least one seed defect, calculating resulting "seed" score as a predefined function of one or more intermediate "seed" scores assigned to the given defect and using the resulting "seed" scores to obtain resulting "review" scores of respective defects; and assigning the obtained resulting "review" scores to respective defects, the resulting "review" scores being usable for selecting defects in the second defect map for review.

In accordance with further aspects of the presently disclosed subject matter, using the CS scores can comprise: applying to the second defect map a set of one or more sampling utilities, each providing for a given defect a respective score, thereby obtaining for the given defect a set of one or more sampling scores, wherein the set of sampling scores comprises a score obtained by using CS scores of defects in the first semiconductor specimen; calculating a resulting "review" score of the given defect as a function of weighed sampling scores; and selecting the defects for review in accordance with the resulting "review" scores.

Among advantages of certain embodiments of the presently disclosed subject matter is reduction of review budget required for an unseen specimen due to usage of prior knowledge acquired for similar specimen(s).

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "representing", "calculating", "generating", "assigning", "selecting" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, FPEI system and parts thereof disclosed in the present application.

The terms "non-transitory memory" and "non-transitory storage medium" used herein should be expansively construed to cover any volatile or non-volatile computer memory suitable to the presently disclosed subject matter.

The term "defect" used in this specification should be expansively construed to cover any kind of abnormality or undesirable feature formed on or within a specimen.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination. In the following detailed description, numerous specific details are set forth in order to provide a thorough understanding of the methods and apparatus.

Figure 1:
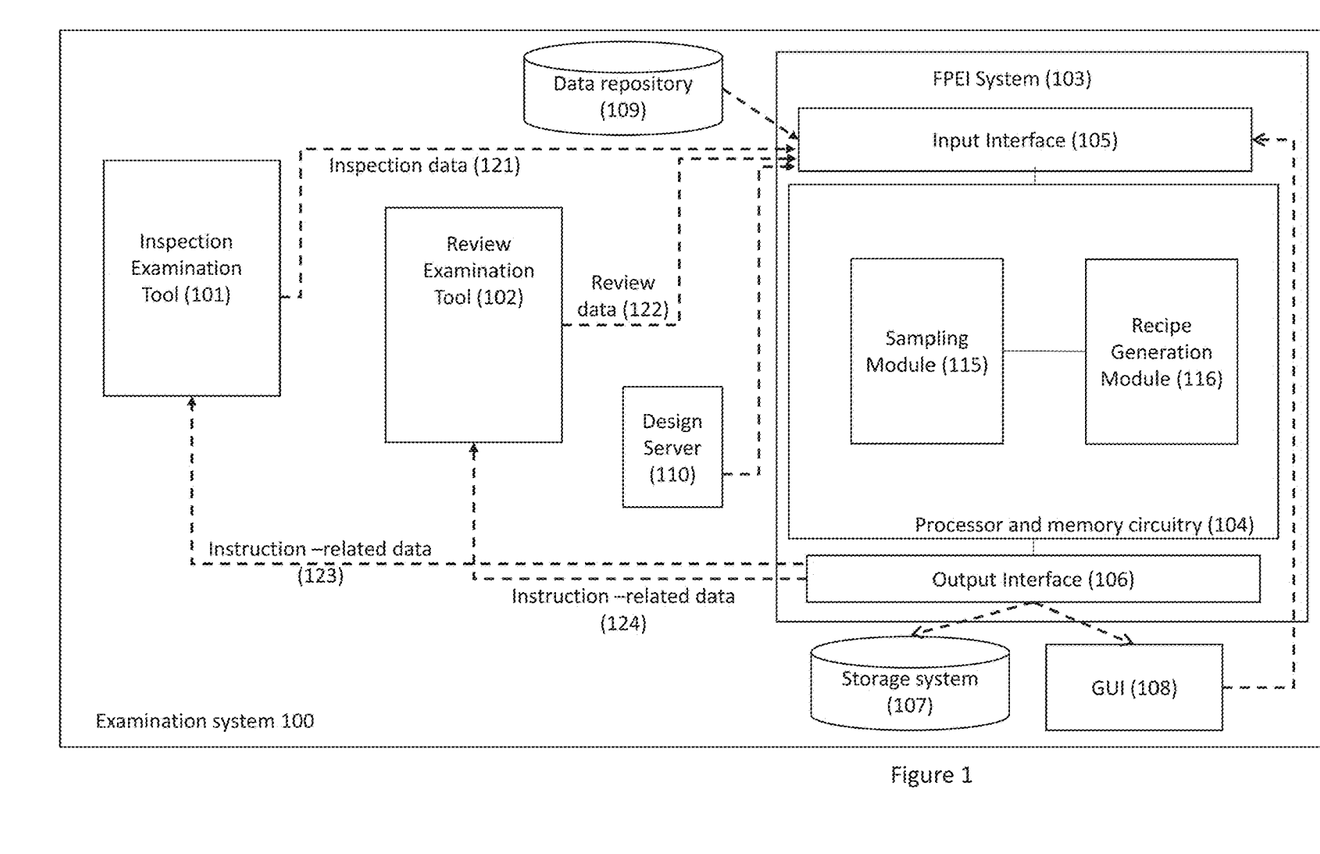
FIG. 1 illustrates a generalized block diagram of an examination system in accordance with certain embodiments of the presently disclosed subject matter.

Bearing this in mind, attention is drawn to FIG. 1 illustrating a generalized block diagram of an examination system in accordance with certain embodiments of the presently disclosed subject matter. The examination system 100 illustrated in FIG. 1 can be used for examination of a specimen (e.g. of a wafer and/or parts thereof) as a part of specimen fabrication. The examination can be a part of the object fabrication and can be carried out during manufacturing the object or afterwards. The illustrated examination system 100 comprises computer-based system 103 capable of automatically determining metrology-related and/or defect-related information using images obtained in specimen fabrication (referred to hereinafter as fabrication process (FP) images) and/or derivatives thereof. The system 103 is referred to hereinafter as FPEI (Fabrication Process Examination Information) system. FPEI system 103 can be operatively connected to one or more inspection examination tools 101 and/or one or more review tools 102. Inspection tools 101 are configured to capture inspection images (typically, at relatively high-speed and/or low-resolution). Review tools 102 are configured to capture review images of at least part of defects detected by inspection tools 101 (typically, at relatively low-speed and/or high-resolution). FPEI system 103 can be further operatively connected to design server 110 and data repository 109.

A specimen can be examined by an inspection tool 101 (e.g. an optical inspection system, low-resolution SEM, etc.). The resulting images and/or derivatives thereof informative of revealed potential defects (collectively referred to hereinafter as inspection data 121) can be transmitted—directly or via one or more intermediate systems—to FPEI system 103. As will be further detailed with reference to FIGS. 2-5, FPEI system is configured to receive, via input interface 105, data produced by inspection tool 101 and/or data stored in one or more data repositories 109 and/or in design server 110 and/or another relevant data depository. Inspection data 121 can be indicative of locations of potential defects and other attributes thereof.

FPEI system is further configured to process the received data and send, via output interface 106, the results (or part thereof) to a storage system 107, to examination tool(s), to a computer-based graphical user interface (GUI) 108 for rendering the results and/or to external systems (e.g. Yield Management System (YMS) of a FAB, recipe node, etc). GUI 108 can be further configured to enable user-specified inputs related to operating FPEI system 103.

As will be further detailed with reference to FIGS. 2-5, FPEI system can be configured to process the received inspection data (optionally together with other data as, for example, design data and/or defect classification data) to select potential defects for review. It is noted that the potential defects for review are referred to hereinafter also as defects for review.

FPEI system can send the processing results (e.g. instruction-related data 123 and/or 124) to any of the examination tool(s), store the results (e.g. defect classification) in storage system 107, render the results via GUI 108 and/or send to an external system (e.g. to YMS, recipe node, etc.).

The specimen can be further examined by review tool 102. A subset of potential defect locations selected for review in accordance with data generated by FPEI can be reviewed by a scanning electron microscope (SEM) or Atomic Force Microscopy (AFM), etc. The resulting data (referred to hereinafter as review data 122) informative of review images and/or derivatives thereof can be transmitted—directly or via one or more intermediate systems—to FPEI system 103 and can be used for further selection of potential defects for review, classifying the reviewed defects, etc.

FPEI system 103 comprises a processor and memory circuitry (PMC) 104 operatively connected to a hardware-based input interface 105 and to a hardware-based output interface 106. PMC 104 is configured to provide processing necessary for operating FPEI system further detailed with reference to FIGS. 2-5 and comprises a processor (not shown separately) and a memory (not shown separately). The processor of PMC 104 can be configured to execute several functional modules in accordance with computer-readable instructions implemented on a non-transitory computer-readable memory comprised in the PMC. Such functional modules are referred to hereinafter as comprised in the PMC. Functional modules comprised in the PMC include sampling module 115 configured to select, based on processing at least part of the data received by FPEI, potential defects for high-resolution review, and to generate respective data informative of the selection. Optionally, PMC can comprise recipe generation module 116 configured to generate a recipe (or part thereof) for a high resolution tool in accordance with data generated by sampling module 115. Operation of FPEI system 103, PMC 104 and the functional blocks therein will be further detailed with reference to FIGS. 2-5.

Those skilled in the art will readily appreciate that the teachings of the presently disclosed subject matter are not bound by the system illustrated in FIG. 1; equivalent and/or modified functionality can be consolidated or divided in another manner and can be implemented in any appropriate combination of software with firmware and hardware.

It is noted that the examination system illustrated in FIG. 1 can be implemented in a distributed computing environment, in which the aforementioned functional modules shown in FIG. 1 can be distributed over several local and/or remote devices, and can be linked through a communication network. It is further noted that in other embodiments at least part of examination tools 101 and/or 102, data repositories 109, storage system 107 and/or GUI 108 can be external to the examination system 100 and operate in data communication with FPEI system 103 via input interface 105 and output interface 106. FPEI system 103 can be implemented as stand-alone computer(s) to be used in conjunction with the examination tools. Alternatively, the respective functions of FPEI system can, at least partly, be integrated with one or more examination tools, process control tools, recipe generation tools, systems for automatic defects review and/or classification, and/or other systems related to examination.

For purpose of illustration only, the following description is provided for wafers. Those skilled in the art will readily appreciate that the teachings of the presently disclosed subject matter are, likewise, applicable to other semiconductor specimens.

Figure 2:
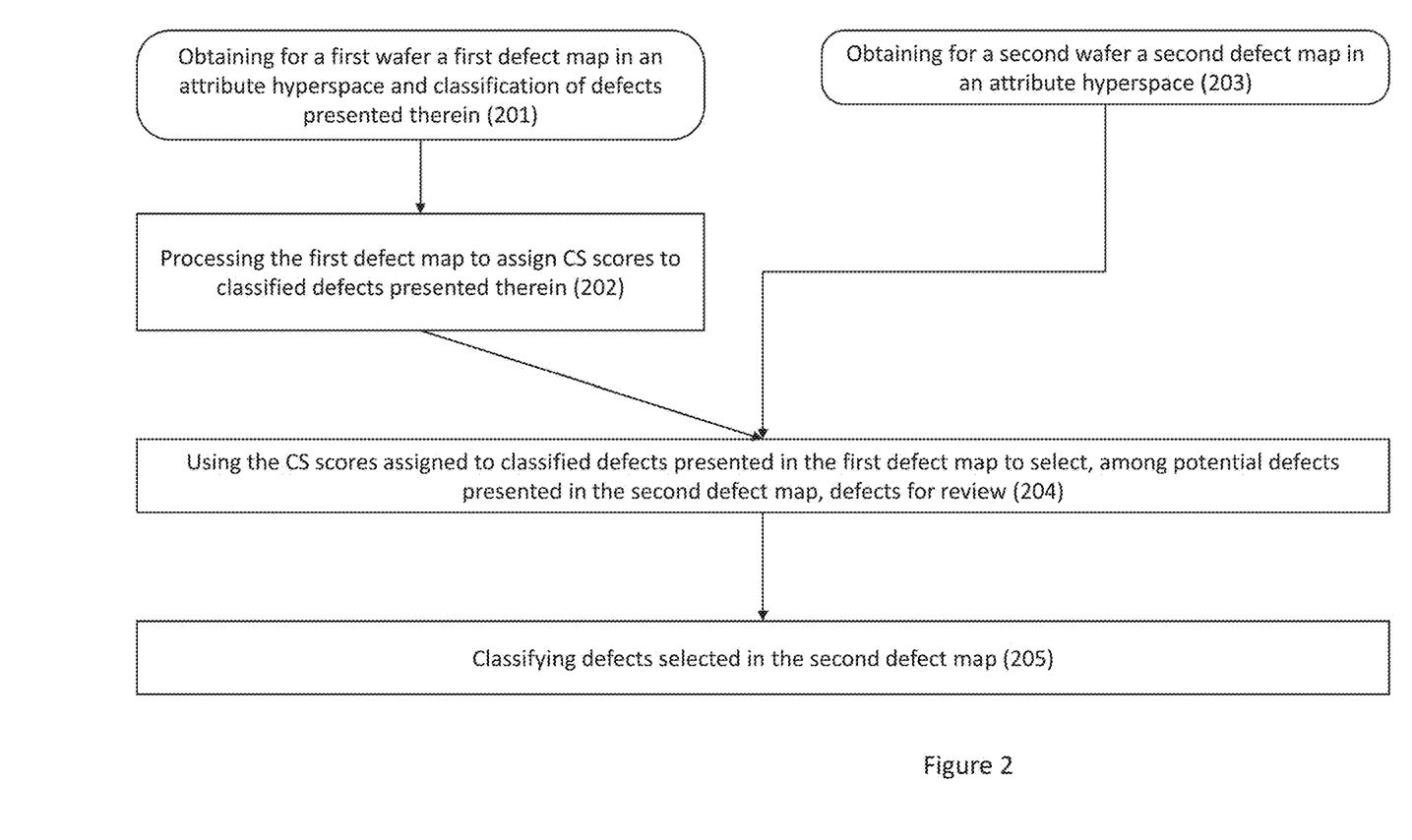
FIG. 2 illustrates a generalized flow-chart of classifying defects in accordance with certain embodiments of the presently disclosed subject matter.

Referring to FIG. 2, there is illustrated a generalized flow-chart of classifying defects. In accordance with certain embodiments of the presently disclosed subject matter, results of classifying defects in one wafer are usable for another wafer for selecting defects to be reviewed.

FPEI system 103 receives low-resolution image data informative of potential defects in a first wafer. Such data include physical locations of potential defects and other defect attributes and can be presented in an attribute hyperspace.

Defect attributes can be related to an examination tool and/or examination process, and can be determined by an examination tool or derived from results generated by an examination tool, or can be derived from design data and/or otherwise computed and/or measured.

By way of non-limiting example, defect attributes can be representative of pixel-related data of a defect and/or vicinity thereof; characteristics related to used sensing elements (e.g. dynamic range, sensitivity threshold, bias, etc.); characteristics related to a used scanning scheme (e.g. scanning scheme accuracy, location of potential defect in relation to a scan line, scanning scheme mechanical noises, etc.); data related to applied illumination conditions (e.g. intensity of light source, frequency of radiation, polarization of light source, speckles, temperature of the object or its surroundings, position of potential defect in relation to an optical axis of the illumination path, etc.); data related to applied collection conditions (e.g. attenuation of a collection path, aberrations of the collection path, position of defect candidate in relation to an optical axis of the collection path, etc.); data related to manufacturing history of the inspected wafer (e.g. process step, process tool, etc.); design related information (e.g. reference geometry, material specifications, regions of interest, etc.) and/or the like.

A data structure representing defects in a K-dimensional attribute hyperspace (each attribute selected for presentation is associated with a respective dimension) in accordance with respectively associated values of defect attributes, is referred to hereinafter as a defect map. Processing data associated with defects represented in a defect map is referred to hereinafter as processing the defect map. Defects presented in the defect map are referred to hereinafter also as defects in the defect map.

Optionally, FPEI can generate a defect map in accordance with a predefined set of attributes and values of respective attributes comprised in the received low-resolution image data. Alternatively, the received low-resolution image data can comprise a respective defect map derived for the predefined set of attributes.

FPEI further obtains data informative of classes of potential defects revealed in the first wafer. Some of the potential defects may be classified as non-defects, some may be classified to one or more classes of defects of interest (DOI) and some may be classified to one or more classes of that are not of interest. The classes of interest may be defined by a user and/or can be defined automatically. The data informative of classes of presented defects can be received from an external system via interface 105, from a user via GUI 108 and/or generated by FPEI system itself.

Thus, FPEI obtains (201), for a first wafer, a first defect map and classification of at least part of the defects presented therein. The received data can be stored in PMC 104 and/or in storage system 107 for later processing. FPEI system (e.g. sampling module 115) processes the first defect map to assign (202) to at least part of the classified defects, "cluster seed" scores. The "cluster seed" score (referred to hereinafter also as a CS score) of a defect classified to a certain class is indicative of a number of neighboring defects classified to the same class. By way of non-limiting example, the number of neighboring defects can be defined as indicative of a number of defects of the same class among a predefined number (e.g. 50) of the closest neighbors in the defect map and/or a number of defects of the same class within a predefined distance in the attribute hyperspace. It is noted that a group of classes (e.g. DOI) can be considered as a class with regard to the "cluster seed score" definition and usage.

Figure 3A:
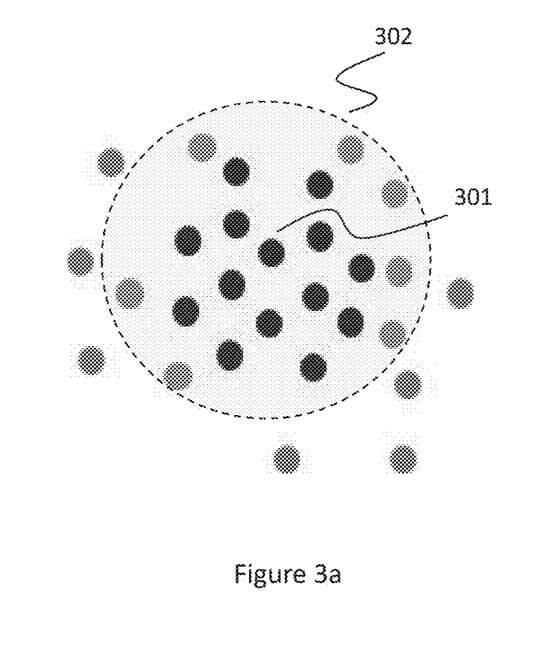
FIGS. 3a and 3b schematically illustrate sections of an exemplified two-dimensional defect map.
Figure 3B:
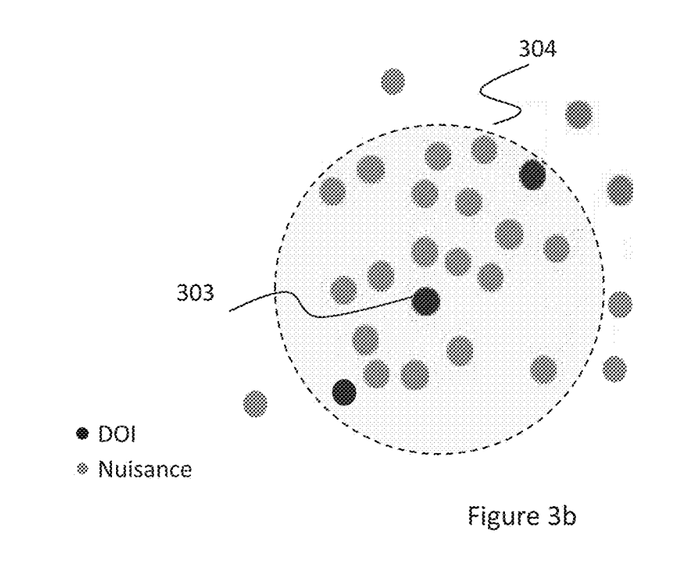

Referring to FIGS. 3a and 3b, there are schematically illustrated two sections of an exemplified two-dimensional defect map. Defects presented in the map are classified into a defects of interest (DOI) group of classes, and into a nuisance group of classes. By way of non-limiting example, the CS score of a given defect can be calculated as a portion of DOI defects among all defects presented in a vicinity of the given defect; vicinity can be characterized by a predefined distance from the given defect. For example, the CS score of classified as a DOI defect 301 can be calculated as equal to 0.65 (13 DOI defects among 20 defects within vicinity illustrated by dotted circle 302). Likewise, the CS score of classified as DOI defect 303 can be calculated as equal to 0.1 (2 DOI defects among 20 defects within the vicinity illustrated by dotted circle 304). It is noted that the CS score can be calculated using any appropriate function providing a score indicative of a number of neighboring defects classified to the same class, and is not limited by the example illustrated above.

Referring back to FIG. 2, data indicative of CS scores of at least part of the classified defects presented in the first defect map can be stored in PMC 104 and/or in storage system 107 for later processing. As will be further detailed with reference to FIGS. 4-5, upon obtaining (203) a second defect map for a second wafer, FPEI system (e.g. sampling module 115) uses the CS scores assigned to the classified defects presented in the first defect map to select (204), among potential defects presented in the second defect map, defects for review.

Selecting, in the second defect map, defects for review, comprises assigning scores to defects presented therein, and selecting defects matching a predefined score-related criterion. By way of non-limiting example, such criterion can specify a number of top-ranked defects to be selected in accordance with batch size for review. Such assignment can be provided with the help of a CS score-based utility.

In accordance with certain embodiments of the presently disclosed subject matter, selecting defects in the second wafer for review can be provided based, merely, on the scores provided by CS score-based utility. In alternative embodiments, the assigned scores used for defect ranking for further selection can be provided by applying a set of sampling utilities, the set including CS score-based utility. In such a case, the assigned score can be calculated as a function of the scores (e.g. average, weighted average, etc.) provided by each of the applied utilities.

Thus, using CS scores can comprise obtaining for a given defect a set of sampling scores by applying to the second defect map a set of two or more sampling utilities each providing for the given defect a respective score; and calculating a resulting "review" score of the given defect as a function of weighed sampling scores, wherein the set of sampling scores comprises a score (referred to hereinafter also as a "seed" score) obtained by using CS scores of defects in the first wafer.

The first wafer and the second wafer shall fit a similarity criterion (such wafers are referred to hereinafter as "similar" wafers). By way of non-limiting example, similarity between wafers can be estimated using any discriminating function between distributions. e.g. Kullback Leibler divergence $$D_{KL}(P||Q) = \int_{-\infty}^{\infty} p(x) \log \frac{p(x)}{q(x)} dx,$$

where $p(x), q(x)$ are the estimated probability density functions calculated for defect maps of respective wafers. The larger the value of $D_{KL}$, the more dissimilar is the pair of wafers. Accordingly, two wafers can be considered as fitting a similarity criterion when $D_{KL}$ is less than a predefined threshold. It is noted that, optionally, the similar first wafer and the second wafer can be of the same design, and the first and the second defect maps can be generated to the same set of attributes with values acquired for the same stage of the manufacturing process.

Upon review, the selected defects can be classified (205) by FPEI and/or by a user and/or by an external classifier.

CS score-based utility can be generated by FPEI (e.g. by recipe module 116), stored in storage system 107 and/or an external recipe node and can be called up prior to or when executing sampling of the second wafer. Optionally, the generated utility can be included in a sampling recipe. Alternatively, the utility can be generated during the sampling process using the "cluster seed scores" previously assigned to defects presented in the first feature map and stored in FPEI system and/or externally.

Figure 4:
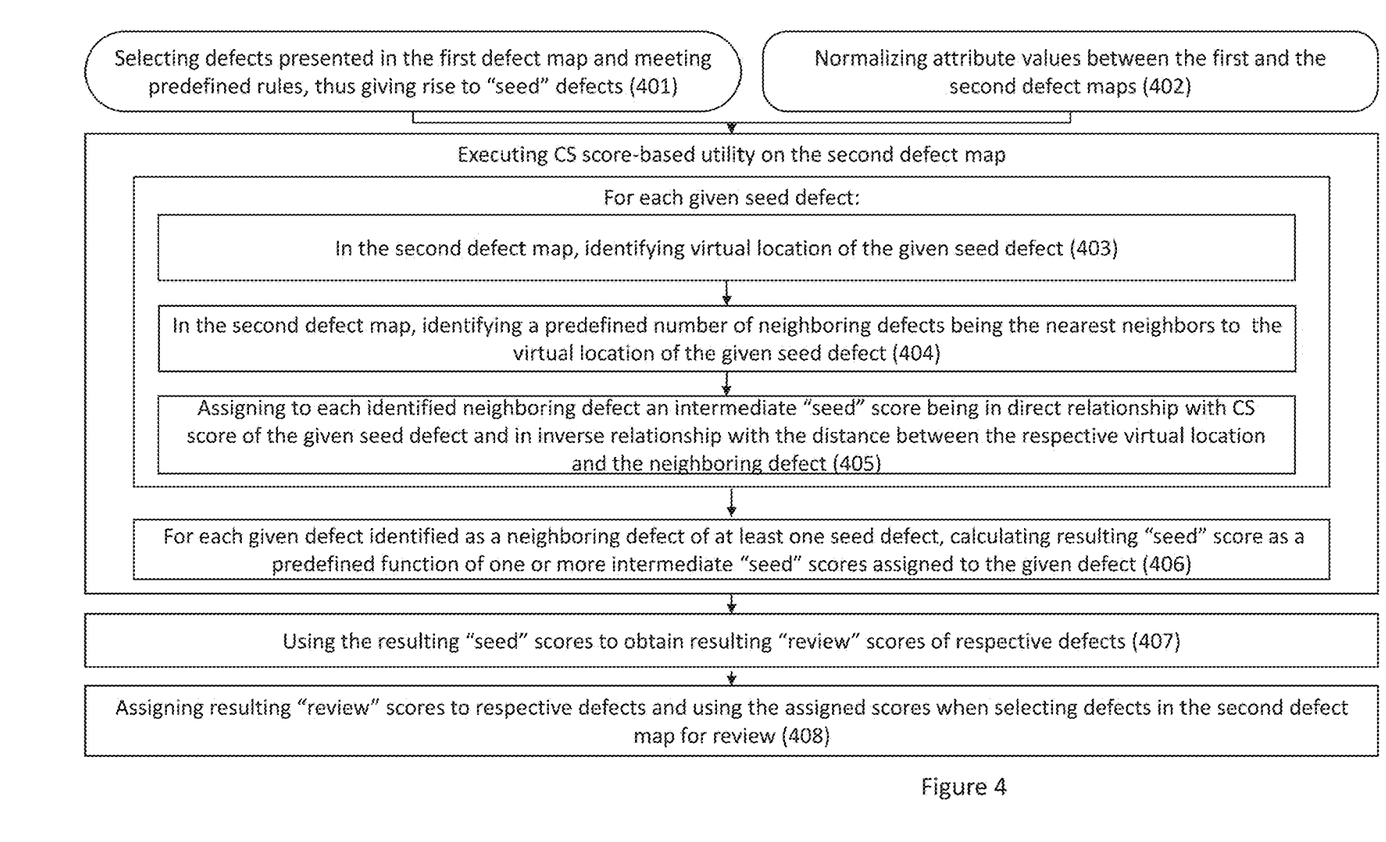
FIG. 4 illustrates a generalized flowchart of selecting defects for review in accordance with certain embodiments of the presently disclosed subject matter.

FIG. 4 illustrates a generalized flowchart of selecting defects for review in accordance with certain embodiments of the presently disclosed subject matter.

Prior to selecting defects in the second wafer for review, FPEI system selects (401), among defects presented in the first defect map, defects that are usable for the second wafer's sampling; such defects in the first defect map are referred to hereinafter as "seed" defects. Selection of seed defects is provided in accordance with predefined rules. The predefined rules include specifying one or more classes of interest (e.g. particles, pattern defects, micro-scratches, all DOI, etc.). The predefined rules can also specify CS score thresholds to be applied when selecting seed defects, physical areas of interest on the second wafer, maximal number of seed defects, etc. By way of non-limiting example, FPEI can select all DOI defects with assigned CS scores to be used as seed defects.

Additionally, prior to selecting defects in the second wafer for review, FPEI system provides normalization (402) of attribute values between the first and the second defect maps in order to neutralize potential differences in acquisition of respective values.

Upon normalization of defect maps and selecting seed defects from the first defect map, FPEI system (e.g. sampling module 115) runs a CS score-based utility on the second defect map. Using this utility, the FREI system, for each seed defect, identifies (403) in the second defect map a location corresponding to location of the respective seed defect in the first defect map. Such a location in the second defect map corresponding to location of the respective seed defect in the first defect map is referred to hereinafter also as a virtual location. FPEI system further identifies (404) a predefined number (e.g. 20) of neighboring defects being the nearest neighbors to the virtual location of the respective seed defect. This process can be described as virtually embedding seed defect from the first defect map into the second defect map and using nearest neighbor (NN) query for location in the second defect map of such a virtually embedded seed defect (i.e. virtual location).

Further, for each seed defect, FPEI system assigns (405) to each identified neighboring defect an intermediate "seed" score being in direct relationship with the CS score of the given seed defect and in inverse relationship with the distance between the virtual location of the respective seed defect and the respective neighboring defect.

For each given defect identified as a neighboring defect of at least one seed defect, FPEI system calculates (406) a resulting "seed" score. The resulting "seed" score is calculated in accordance with a predefined function (e.g. average, weighted average, etc.) of one or more intermediate "seed" scores assigned to the given defect. The resulting "seed" score is indicative of probability of respective defect to be classified into a defect of respective class (e.g. to be a defect of interest), a higher score being indicative of a higher probability.

FPEI system further obtains the resulting "review" score usable for selecting defects in the second wafer for review. The resulting "review" score can be obtained (407) by specifying the "seed" score as a resulting "review" score. Alternatively, the resulting "review" score can be obtained (407) as a function (e.g. as a weighted average) of the resulting "seed" score and scores provided by one or more other applied utilities. FPEI system assigns (408) the resulting "review" scores to respective defects in the second defect map.

FPEI system further uses the assigned resulting "review" score when selecting defects in the second wafer for review.

Figure 5:
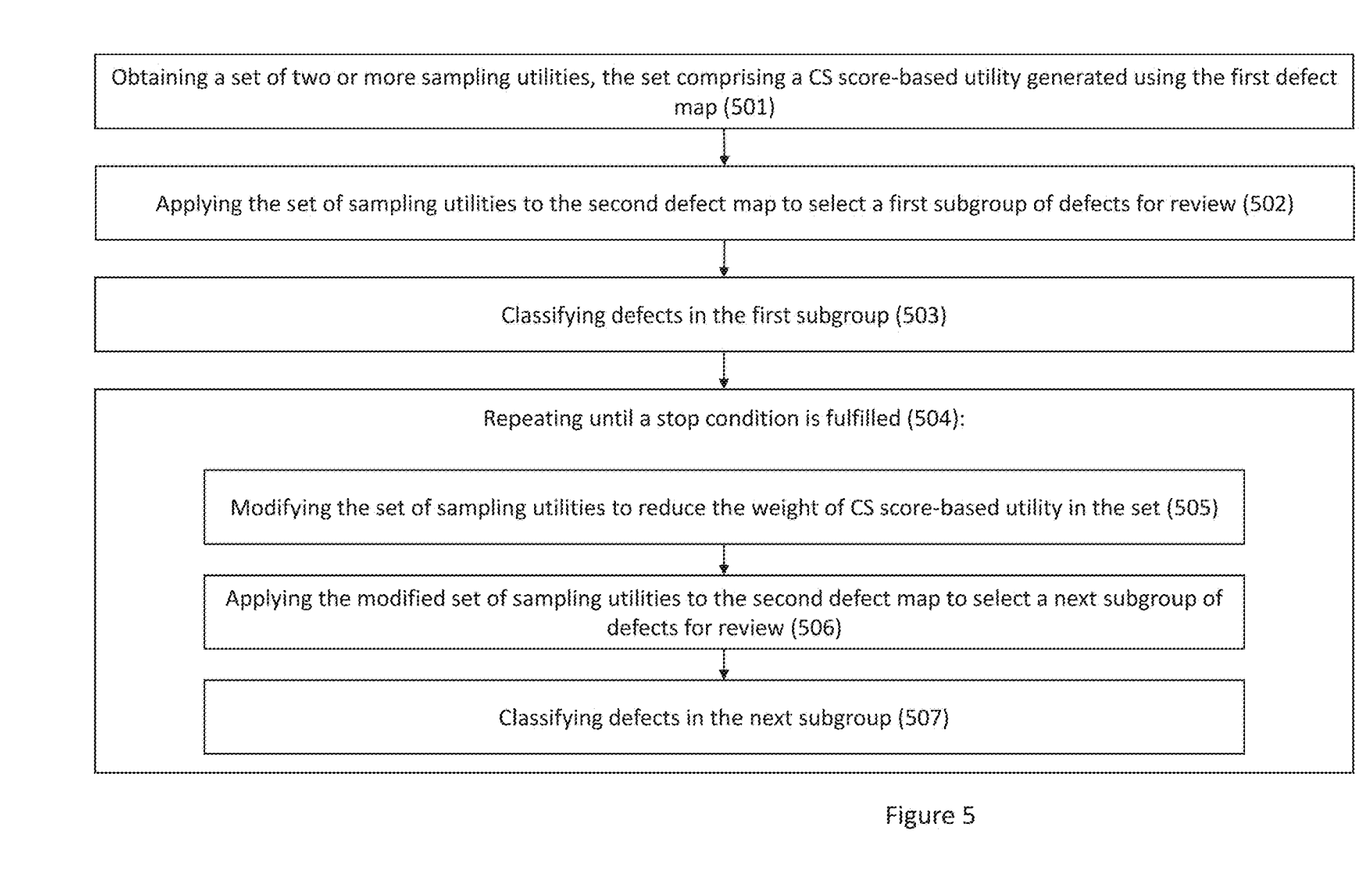
FIG. 5 illustrates a generalized flow-chart of an iterative process of classifying defects in accordance with certain embodiments of the presently disclosed subject matter.

Referring to FIG. 5, there is illustrated a generalized flow-chart of an iterative process of classifying defects using CS score-based utility.

Prior to selecting defects in the second wafer for review, FPEI system obtains (501) a set of two or more sampling utilities, the set comprising a CS score-based utility generated using the first defect map. The set can further comprise utilities for sampling based on anomalies detected in the second defect map, for sampling based on predefined attributes and/or any other utility suitable for selection of defects for review.

The utilities can be can be stored at FPEI and/or at an external recipe node and can be called up when executing sampling of the second wafer. Optionally, the set of utilities can be included in a sampling recipe. Alternatively, at least one of the utilities can be generated by FPEI during the sampling process.

FPEI selects (502) a first subgroup of potential defects for review, the selection provided by applying the set of sampling utilities to the second defect map, and obtains (503) classification results after the selected subgroup is reviewed. The defects in the selected subgroup can be classified by FPEI and/or by a user and/or by an external classifier.

FPEI further repeats (504) the following operations until a stop condition is fulfilled: modifying (505) the set of sampling utilities to reduce the weight of CS score-based utility in the set of sampling utilities; applying the modified set of sampling utilities to the second defect map to select (506) a next subgroup of potential defects for review; and obtaining classification results for defects in the next subgroup (507).

By way of non-limiting example, the stop condition can be fulfilled when the obtained classification results have a purity level exceeding a purity threshold.

The weight of CS score-based utility in the set of sampling utilities is indicative of influence of the resulting "seed" score on selecting defects for review.

By way of non-limiting example, when selecting the first subgroup of defects for review, the weight of CS score-based utility in the set of sampling utilities can be configured as equal to 100% (i.e. the selection decision can be provided solely in accordance with the resulting "seed" scores assigned by the CS score-based utility), while this weight can be exponentially reduced for selection of each next subgroup. Optionally, when the weight of the CS score-based utility is lower than a predefined criteria, this utility can be removed from the set. By way of another non-limiting example, the weight of CS score-based utility can be changed dynamically according to results of the iterative process, and not necessarily in a pre-defined manner.

It is noted that modifying the set of sampling utilities also includes modifying the way of calculating the resulting "review" score (and/or the weights of scores from different utilities in the resulting "review" score) with no changes in the utilities themselves and/or the way of their execution.

Figure 6:
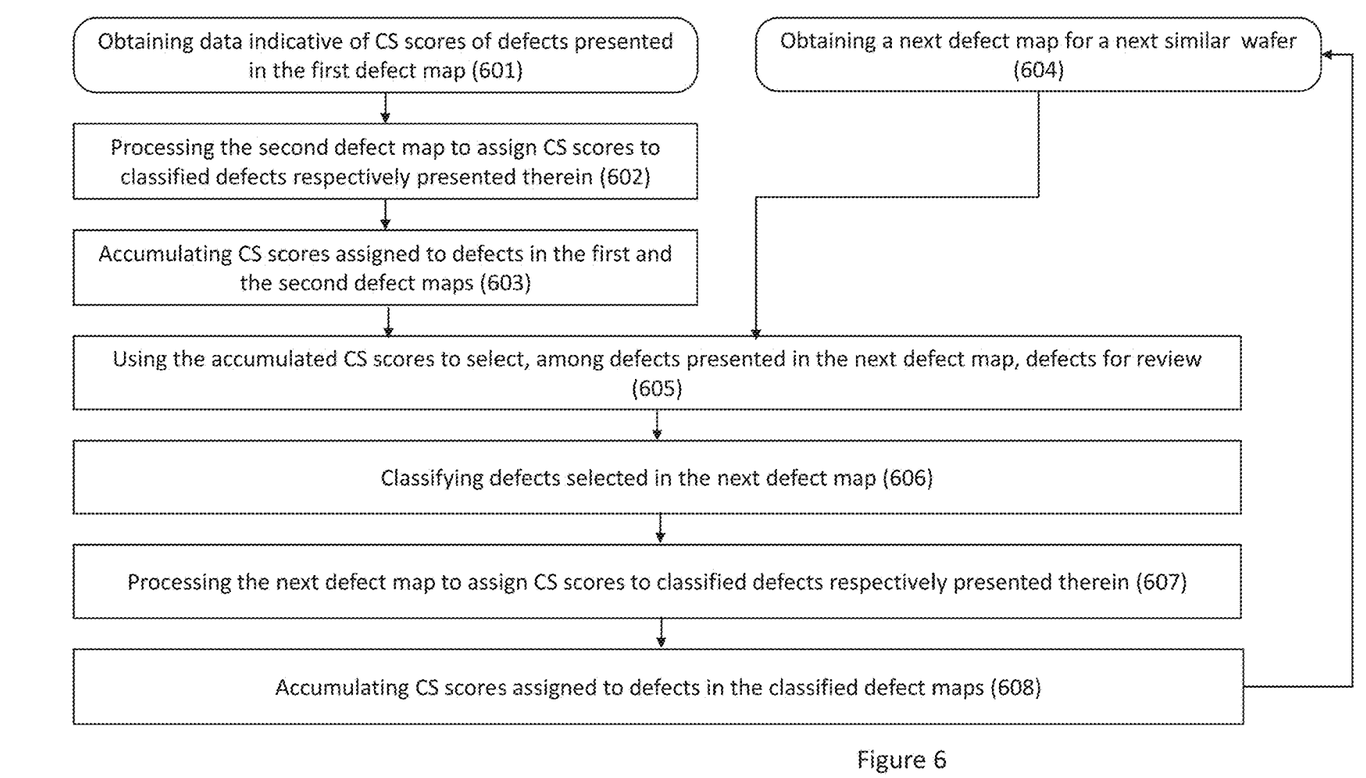
FIG. 6 illustrates a generalized flow-chart of accumulative usage of classified wafers in accordance with certain embodiments of the presently disclosed subject matter

Referring to FIG. 6, there is illustrated a generalized flow-chart of accumulative usage of classified wafers in accordance with certain embodiments of the presently disclosed subject matter.

Upon classifying defects presented in the second defect map, FPEI system processes the second defect map to assign (602) CS scores to classified defects presented therein. FPEI system further accumulates (603) the previously obtained (601) CS scores of defects presented in the first defect map, and the CS scores assigned to defects presented in the second defect map.

Upon obtaining (604) for a next similar wafer, a next defect map, FPEI system further uses the accumulated CS scores to select (605), among potential defects presented in the next defect map, defects for review. After defects selected in the next defect map for review are classified (606), FPEI system processes the next defect map to assign (607) CS scores to classified defects respectively presented therein, and accumulates CS scores assigned to defects in the classified similar wafers. By way of non-limiting example, CS scores can be accumulated by stacking the defect maps into a single defect map and recalculating the cluster seed scores on the unified map. By way of alternative non-limiting example, scores can be accumulated by "virtually embedding" the first defect map into each next defect map and further accumulating the propagated score.

Obtained defect maps, assigned CS scores and/or accumulated CS scores can be accommodated in a database stored in PMC 104 and/or in storage system 107 and/or an external storage.

Thus, defects in a further next wafer can be selected using the score accumulated over previous similar wafers. This way, small clusters undetectable in a single wafer can be significantly amplified if repeated across some other similar wafers.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. An examination system comprising:
a memory; and
a processor, operatively coupled with the memory, to:
upon obtaining a first defect map representing defects in a first semiconductor specimen in an attribute hyperspace, process the first defect map to assign cluster-seed (CS) scores to at least part of classified defects presented in the first defect map, wherein a CS score of a given defect of the classified defects in the first defect map is indicative of a number of neighboring defects in the first defect map that are classified to the same class as the given defect;
upon obtaining a second defect map representing defects in a second semiconductor specimen in the attribute hyperspace, use the CS scores assigned to the at least part of classified defects presented in the first defect map to select, among defects presented in the second defect map, defects for review; and review the selected defects in the second defect map for classification of the selected defects.

2. The examination system of claim 1, wherein to use the CS scores, the processor is further to:
   a. apply to the second defect map a set of one or more sampling utilities, each sampling utility providing for a given defect a respective score, thereby obtaining for the given defect a set of one or more sampling scores, wherein the set of sampling scores comprises a score obtained by using CS scores of defects in the first semiconductor specimen and provided by a CS score-based utility;
   b. calculate a resulting "review" score of the given defect as a function of weighed sampling scores; and
   c. select the defects for review in accordance with the resulting "review" score.

3. The examination system of claim 2, wherein the processor is further to use the CS scores assigned to the at least part of classified defects presented in the first defect map to generate a sampling recipe usable for selecting defects in the second semiconductor specimen for reviewing by an examination tool.

4. The examination system of claim 3, wherein the processor is further to generate the CS score-based utility and to use the generated CS score-based utility to generate the sampling recipe.

5. The examination system of claim 1, wherein the processor is further to:
   a. upon obtaining data informative of classification of defects presented in the second defect map, assign respective CS scores to classified defects presented in the second defect map;
   b. accumulate CS scores assigned to defects in the first and the second defect maps;
   c. use the accumulated CS scores to select, among defects presented in a next defect map, defects for review;
   d. upon obtaining data informative of classification of defects presented in the next defect map, process the next defect map to assign CS scores to the classified defects respectively presented therein; and
   e. accumulate CS scores assigned to defects in the first defect map, the second defect map and the next defect map, the accumulated CS scores usable for selecting defects for review in a further next defect map.

6. The examination system of claim 1, wherein to select, among defects presented in the second defect map, defects for review, the processor is further to:
   a. select, among defects presented in the first defect map, defects having an assigned CS score and meeting one or more predefined rules, thus giving rise to seed defects;
   b. for each given seed defect:
      i. identify a virtual location of the given seed defect in the second defect map;
      ii. identify in the second defect map a predefined number of neighboring defects being the nearest neighbors to the virtual location of the given seed defect;
      iii. assign to each identified neighboring defect an intermediate "seed" score being in direct relationship with the CS score of the given seed defect and in inverse relationship with a distance between the respective virtual location and the neighboring defect;
   c. for each defect identified in the second defect map as a neighboring defect of at least one seed defect, calculate a resulting "seed" score as a predefined function of one or more intermediate "seed" scores assigned to the given defect and using the resulting "seed" scores to obtain resulting "review" scores of respective defects; and
   d. assign the obtained resulting "review" scores to respective defects, the resulting "review" scores being usable for selecting defects in the second defect map for review.

7. The examination system of claim 1 further comprising a recipe node operatively connected to an examination tool, wherein the processor is implemented as a part of the recipe node.

8. A method comprising:
   processing a first defect map obtained for a first semiconductor specimen to assign cluster-seed (CS) scores to at least part of the classified defects presented in the first defect map therein, wherein a CS score of a given defect of the classified defects in the first defect map is indicative of a number of neighboring defects in the first defect map that are classified to the same class as the given defect;
   upon obtaining a second defect map for a second semiconductor specimen, using, by a processor, the CS scores assigned to the at least part of the classified defects presented in the first defect map to select, among defects presented in the second defect map, defects for review, wherein the first defect map and the second defect map present respective defects in an attribute hyperspace; and
   reviewing the selected defects in the second defect map to obtain classified defects in the second semiconductor specimen.

9. The method of claim 8, wherein selecting, in the second defect map, defects for review comprises assigning scores to defects presented therein and selecting defects matching a predefined score-related criterion, wherein the scores are calculated using the CS scores assigned to the at least some of classified defects presented in the first defect map.

10. The method of claim 9, wherein the score-related criterion specifies a number of top-ranked defects to be selected in accordance with a predefined number of defects to be selected for review.

11. The method of claim 8, wherein using the CS scores comprises:
   a. applying to the second defect map a set of one or more sampling utilities each providing for a given defect a respective score, thereby obtaining for the given defect a set of one or more sampling scores, wherein the set of sampling scores comprises a score obtained by using CS scores of defects in the first semiconductor specimen;
   b. calculating a resulting "review" score of the given defect as a function of weighed sampling scores; and
   c. selecting the defects for review in accordance with the resulting "review" score.

12. The method of claim 11, further comprising:
   a. applying to the second defect map the set of sampling utilities to select a first subgroup of defects for review, wherein the set of sampling utilities comprises two or more sampling utilities;
   b. upon classifying defects in the first subgroup, repeating until a stop condition is fulfilled:

i. modifying the set of sampling utilities to reduce the weight of the score obtained by using CS scores of defects in the first semiconductor specimen;
ii. applying to the second defect map a modified set of sampling utilities to select a next subgroup of defects for review; and
iii. classifying defects in the next subgroup.

13. The method of claim 12, wherein the weight of the score obtained by using CS scores of defects in the first semiconductor specimen is equal to 100% when selecting the first subgroup of defects for review, and wherein the weight is exponentially reduced for selection of each next subgroup.

14. The method of claim 8, wherein selecting, among defects presented in the second defect map, defects for review comprises:
a. selecting, among defects presented in the first defect map, defects having an assigned CS score and meeting one or more predefined rules, thus giving rise to seed defects;
b. for each given seed defect:
i. identifying a virtual location of the given seed defect in the second defect map;
ii. identifying in the second defect map a predefined number of neighboring defects being the nearest neighbors to the virtual location of the given seed defect;
iii. assigning to each identified neighboring defect an intermediate "seed" score being in direct relationship with the CS score of the given seed defect and in inverse relationship with the distance between the respective virtual location and the neighboring defect;
c. for each defect identified in the second defect map as a neighboring defect of at least one seed defect, calculating resulting "seed" score as a predefined function of one or more intermediate "seed" scores assigned to the given defect and using the resulting "seed" scores to obtain resulting "review" scores of respective defects; and
d. assigning the obtained resulting "review" scores to respective defects, the resulting "review" scores being usable for selecting defects in the second defect map for review.

15. The method of claim 14, wherein the one or more predefined rules specify that the seed defects are selected among defects classified as defects of interest (DOI) having CS scores meeting a threshold criteria.

16. The method of claim 8, further comprising:
a. upon classifying defects presented in the second defect map, assigning to said classified defects respective CS scores;
b. accumulating CS scores assigned to defects in the first and the second defect maps;
c. using the accumulated CS scores to select, among defects presented in a next defect map, defects for review;
d. upon classifying defects in the next defect map, processing the next defect map to assign CS scores to the classified defects respectively presented therein; and
e. accumulating CS scores assigned to defects in the first defect map, the second defect map and the next defect map, the accumulated CS scores usable for selecting defects for review in a further next defect map.

17. A non-transitory computer readable medium comprising instructions that, when executed by a processor, cause the processor to perform operations comprising:
processing a first defect map obtained for a first semiconductor specimen to assign cluster-seed (CS) scores to at least part of the classified defects presented in the first defect map, wherein a CS score of a given defect of the classified defects in the first defect map is indicative of a number of neighboring defects in the first defect map that are classified to the same class as the given defect;
upon obtaining a second defect map for a second semiconductor specimen, using the CS scores assigned to the at least part of classified defects presented in the first defect map to select, among defects presented in the second defect map, defects for review, wherein the first defect map and the second defect map present respective defects in an attribute hyperspace; and
reviewing the selected defects in the second defect map to obtain classified defects in the second semiconductor specimen.

18. The non-transitory computer readable medium of claim 17, wherein selecting, among defects presented in the second defect map, defects for review comprises:
a. selecting, among defects presented in the first defect map, defects having an assigned CS score and meeting one or more predefined rules, thus giving rise to seed defects;
b. for each given seed defect:
i. identifying a virtual location of the given seed defect in the second defect map;
ii. identifying, in the second defect map, a predefined number of neighboring defects being the nearest neighbors to the virtual location of the given seed defect;
iii. assigning to each identified neighboring defect an intermediate "seed" score being in direct relationship with CS score of the given seed defect and in inverse relationship with the distance between the respective virtual location and the neighboring defect;
c. for each defect identified in the second defect map as a neighboring defect of at least one seed defect, calculating a resulting "seed" score as a predefined function of one or more intermediate "seed" scores assigned to the given defect, and using the resulting "seed" scores to obtain resulting "review" scores of respective defects; and
d. assigning the obtained resulting "review" scores to respective defects, the resulting "review" scores being usable for selecting defects in the second defect map for review.

19. The non-transitory computer readable medium of claim 17, wherein using the CS scores comprises:
a. applying to the second defect map a set of one or more sampling utilities each providing, for a given defect, a respective score, thereby obtaining for the given defect a set of one or more sampling scores, wherein the set of sampling scores comprises a score obtained by using CS scores of defects in the first semiconductor specimen;
b. calculating a resulting "review" score of the given defect as a function of weighed sampling scores; and
c. selecting the defects for review in accordance with the resulting "review" scores.

20. The non-transitory computer readable medium of claim 19, the operations further comprising:
a. applying to the second defect map the set of sampling utilities to select a first subgroup of defects for review, wherein the set of sampling utilities comprises two or more sampling utilities;

b. upon classifying defects in the first subgroup, repeating until a stop condition is fulfilled:
  i. modifying the set of sampling utilities to reduce the weight of the score obtained by using CS scores of defects in the first semiconductor specimen;
  ii. applying to the second defect map a modified set of sampling utilities to select a next subgroup of defects for review; and
  iii. classifying defects in the next subgroup.

* * * * *